United States Patent [19]

Nakanishi et al.

[11] Patent Number: 4,510,248

[45] Date of Patent: Apr. 9, 1985

[54] PROCESS FOR CONCENTRATING AND PURIFYING HUMAN URINARY KALLIKREIN

[75] Inventors: Koichiro Nakanishi, Ashiya; Hajime Hiratani, Sennan, both of Japan

[73] Assignee: Japan Chemical Research Co., Ltd., Kobe, Japan

[21] Appl. No.: 509,030

[22] Filed: Jun. 29, 1983

[30] Foreign Application Priority Data

Jun. 30, 1982 [JP] Japan .................. 57-113364

[51] Int. Cl.$^3$ .................. C12N 9/64; C12N 9/48; C12N 9/50
[52] U.S. Cl. .................. 435/226; 435/212; 435/219
[58] Field of Search .................. 435/212, 226, 815

[56] References Cited

U.S. PATENT DOCUMENTS 4,393,140 7/1983 Schutt .................. 435/226

FOREIGN PATENT DOCUMENTS 58-5191 1/1983 Japan .................. 435/226

OTHER PUBLICATIONS

Geiger et al., "Human Urinary Kallikrein", Methods in Enzymology, vol. 80, pp. 466–492 (1981).
Biotechnology and Bioengineering, vol. 20, pp. 87–94 (1978).

Primary Examiner—Lionel M. Shapiro
Attorney, Agent, or Firm—Burgess, Ryan & Wayne

[57] ABSTRACT

Human urinary kallikrein is concentrated and purified by the following procedures; (a) Human urine is contacted with chitosan, a high molecular agglutinant obtained from chitin, at a pH from 4.0 to 7.0, thereby kallikrein is adsorbed on the chitosan and (b) kallikrein is eluted from the chitosan with an aqueous alkaline solution having a pH from 8.0 to 12.0.

7 Claims, No Drawings

PROCESS FOR CONCENTRATING AND PURIFYING HUMAN URINARY KALLIKREIN

This invention relates to a process concentrating and purifying human urinary kallikrein (hereinafter may be abbreviated to "HUKN") from human urine on an industrial scale with high yield and high purity.

Kallikrein is a proteolytic enzyme produced in the body of animals and it decomposes quininogen in serum to form quinine through which exerts pharmacological actions such as the deprssion of blood pressure and the increase of blood circulation.

Thus far, kallikrein has been purified from the pancreas and urine of mammalian animals, especially those of pig origin. Such a conventional kallikrein originated from foreign animals may possibly cause side effect such as antigen antibody reaction in parenteral administration. Due to the fact that HUKN from human urinary source is a homogenous protein, it has no side effect such as antigen antibody reaction. Besides, even if other proteins than HUKN are contained as impurities, their side effect on the human body is rare.

Regarding the concentration and purification of human urinary kallikrein, there are known a process employing silica gel (Japanese patent publication No. 19067/1971), a process employing arginine-Sepharose (Japanese patent application disclosure No. 99191/1980) and a process which employs macroporous anion exchange resin having high degree of cross-linkage and tertiary amino groups as the ion exchange group (Japanese patent application disclosure No. 5515/1975).

It is hard, however, to consider the above-mentioned methods are satisfactory from the view points of purity, recovery rate, cost and simplicity in the procedure.

The present inventors coducted an extensive research for developing a process for obtaining highly purified kallikrein from human urine on an industrial scale with a good yield.

The present inventors carried out comparative research as to the recovery rate and the purification rate of HUKN from urine employing the materials such as respective type of inorganic adsorbent, ion exchanger and protein agglutinant, as described in the following.

Samples of one liter each of the same normal human urine was adsorbed on 5 grams each of the above-mentioned material and then eluted. HUKN acitivity and protein content in the eluate were determined and the recovery rate and specific activity were calculated, thereby results as shown in Table 1 were obtained.

In the Table, adsorbent No. 1 to No. 3 are products of Wako Junyaku K. K. (Osaka, Japan); adsorbent No. is available under the tradename of Wako Gel C-100; adsorbent No. 2 has 200 to 300 meshes (Tyler) of particle size; adsorbent No. 4 is a product of Brown Co., Ltd. (New Hampshire, U.S.A.); adsorbent No. 5 and No. 7 are products of Pharmacia Fine Chemicals AG (Uppsala, Sweden); adsorbent No. 6 is a product of Mitsubishi Chem. Ind., Ltd., (Tokyo, Japan); adsorbent No. 8 is a product of Kyowa Yushi Kogyo K. K. (Chiba, Japan) and is available under the tradename of Flonac-N.

As will be apparent from the results described in the table, chitosan selectively adsorbed HUKN and was superior in rate of recovery and rate of purification. Chitosan is a material produced from chitin by hydrolyzation with conc. alkaline under heating and chitin is obtained from crusts of crustaceous such as crab and shrimps. It is a polysaccharide having a molecular structure of (2-amino-2deoxy-D-glucose)$_n$ and a molecular weight of about 200,00. Chitosan is employed as an effective, nontoxic high molecular agglutinant having particle size of less than 3.5 mm.

TABLE 1-A

| No. | Adsorbent | Adsorption Buffer | pH | Dilution |
|---|---|---|---|---|
| 1 | Silica gel | — | 3.5 | × 1 |
| 2 | Activated alumina | — | 3.5 | × 1 |
| 3 | Kaoline | — | 3.5 | × 1 |
| 4 | DEAE-Cellulose | 0.05 M-Phosphate buffer solution | 7.0 | × 3 |
| 5 | DEAE-Sephadex | 0.05 M-Phosphate buffer solution | 7.0 | × 3 |
| 6 | WA - 30 | 0.2 M-Ammonium chloride buffer solution | 7.0 | × 1 |
| 7 | Arg - Sephadex | 0.05 M-Tris hydrochloric acid buffer solution | 7.5 | × 1 |
| 8 | Chitosan | — | 5.5 | × 1 |

TABLE 1-B

| No. | Elution Eluate | pH | Yield (%) | Purity units/mg (protein) |
|---|---|---|---|---|
| 1 | 2% Aqueous ammonia | | 48 | 14 |
| 2 | " | | 20 | 4 |
| 3 | " | | 43 | 10 |
| 4 | 0.5 M-Phosphate buffer solution | 7.0 | 38 | 8 |
| 5 | 0.5 M-Phosphate buffer solution | 7.0 | 60 | 12 |
| 6 | 0.6 M-Ammonium chloride buffer solution | 7.0 | 31 | 8 |
| 7 | 0.5 M-Tris hydrochloric acid buffer solution containing 0.5 M-sodium chloride | 7.5 | 51 | 10 |
| 8 | 2% Aqueous ammonia | | 70 | 33 |

This invention is based on the above findings and directed to a process which comprises contacting chitosan with human urine at a pH from 4.0 to 7.0 to adsorb kallikrein in the urine on the chitosan, filtering off the chitosan from the urine and eluting kallikrein from the chitosan with an aqueous alkaline solution.

The pH of human urine contacted with chitosan may be adjusted to 4.0–7.0, preferably 5.0.

In general, the amount of chitosan to be employed may be to the extent of 1–10 grams per liter of urine.

By contacting with chitosan, HUKN in the human urine is selectively adsorbed on the chitosan.

This adsorption can be carried out at common temperature.

Then the kallikrein-adsorbed chitosan is filtered and washed sufficiently with water and then HUKN is eluted with an aqueous alkaline solution. The pH of the alkaline solution is desirably within the range of 8.0–12. The preferred examples of such solution are 1N-aqueous ammonia and 0.1 to 0.3M tris hydrochloric acid buffer solution.

The advantage in the use of chitosan is not limited to the selective adsorption of HUKN, but it makes possible to carry out separation, washing and elution procedures of the adsorbent in a shorter period of time than as required in the conventional procedures. Furthermore, for massive treatment of urine, it is advantageous to apply chitosan in the simplification of operations for vacuum filtration, centrifugation or the like.

In order to inactivate hepatitis virus which might infect and contaminate the human urine used in the production of HUKN, HUKN-adsorbed chitosan may be placed in an aqueous solution having pH about 6, subsequently incubated at about 60° C. for not less than 10 hours, and HUKN is eluted from the chitosan.

When ion exchanger or inorganic adsorbent is employed as an adsorbent, it is necessary to wash the adsorbent with acid or alakline solution and then heat the adsorbent for activation in order to regenerate the adsorbent after elution. However, in the case of employing chitosan in this invention, the adsorbent can be reused by simply washing the adsorbent after elution.

The following examples are further illustrative of this invention.

EXAMPLE 1

While strring, 2N-hydrochloric acid was added to 10 liters of human urine from healthy male adults to adjust pH to 5.5. One hundred grams of chitosan was added to the urine, stirred for one hour to thereby adsorb HUKN, and then, HUKN-adsorbed chitosan was obtained by filtration. Subsequently, the chitosan was sufficiently washed with pure water, eluted with 1N-aqueous ammonia, and filtered to obtain 400 ml of HUKN extract.

The total activity of HUKN was 1,368 units (recovery rate of 72%) and the purity thereof was 34 units/mg (protein).

EXAMPLE 2

While stirring, 2N-hydrochloric acid was added to 10 liters of human urine from healthy male adults to adjust pH to 4.5. Fifty grams of chitosan was contacted with the urine and stirred for one hour to thereby adsorb HUKN. Filtration was carried out and HUKN-adsorbed chitosan was obtained. Subsequently, the chitosan was sufficiently washed with pure water and 300 ml of HUKN was extracted with 0.3M-tris-hydrochloric acid buffer solution (pH 10.0).

The total activity of HUKN thus obtained was 1,350 units (recovery rate of 71%) and the purity thereof was 33 units/mg (protein).

EXAMPLE 3

While stirring, 2N-hydrochloric acid was added to 10 liters of human urine from healthy male adults to adjust pH to 6.5. One hundred grams of chitosan was contacted and stirred for one hour to thereby adsorb HUKN. Filtration was carried out and HUKN-adsorbed chitosan was obtained. Subsequently, the chitosan was sufficiently washed with pure water and extracted with 0.1M-tris-hydrochloric acid buffer solution (pH 8.0). Filtration was carried out and 400 ml of HUKN extract was thus obtained.

The total activity of HUKN was 1,225 units (recovery rate of 72%) and the purity thereof was 27 units/mg (protein).

EXAMPLE 4

While stirring, 2N-hydrochloric acid was added to 10 liters of human urine from healthy male adults to adjust pH to 5.5. Fifty grams of chitosan was contacted and stirred for one hour to thereby adsorb HUKN. Filtration was carried out and HUKN-adsorbed chitosan was obtained. Subsequently, the chitosan was washed with 0.05M-phosphate buffer solution (pH 6.0) containing 0.15M-sodium chloride and filtered. Three hundred ml of the same buffer solution was added to the filtered chitosan and incubation was carried out at 60° C. for 10 hours. Then the chitosan was separated by filtration and eluted with 1.5N-aqueous ammonia. Filtration was carried out and 450 ml of HUKN extract solution was thus obtained.

The total activity of HUKN was 1,085 units (recovery rate of 65%) and the purity thereof was 37 units/mg (protein).

EXAMPLE 5

While stirring, 2N-hydrochloric acid was added to 10 liters of human urine from healthy male adults to adjust pH to 5.0. One hundred grams of chitosan was contacted and stirred for one hour to thereby adsorb HUKN. Filtration was carried out and HUKN-adsorbed chitosan was obtained. Subsequently, the chitosan was sufficiently washed with pure water and extracted with 1N-aqueous ammonia. Filtration was carried out and 400 ml of HUKN extract solution was thus obtained.

The total activity of HUKN was 1,260 units (recovery rate of 71%) and the purity thereof was 33 units/mg (protein).

The above HUKN extract was dialyzed against 0.05M-phosphate buffer solution and adsorbed on DEAE-Cellulose column (diameter 3 cm, height 20 cm) which was previously buffered with the above-mentioned buffer solution. After washing with the said buffer solution, elution was carried out with 0.05M-phosphate buffer solution (pH 7.0) containing 0.4M-sodium chloride and 51 ml of HUKN solution was thereby obtained.

The total activity of HUKN was 1,070 units (recovery rate of 71%) and the purity thereof was 310 units/mg (protein).

EXAMPLE 6

While stirring, 2N-hydrochloric acid was added to 10 liters of human urine from healthy male adults to adjust to pH 5.0. One hundred grams of chitosan was contacted and stirred for one hour to thereby adsorb HUKN. Filtration was carried out and HUKN-adsorbed chitosan was obtained. Subsequently, the chitosan was sufficiently washed with pure water and extracted with 0.2M-tris-hydrochloric acid buffer solution (pH 9.0). Filtration was carried out and 300 ml of HUKN extract solution was thus obtained.

The total activity of HUKN was 1,385 units (recovery rate of 71%) and the purity thereof was 32 units/mg (protein).

Two hundred grams of ammonia sulfate was added to the above HUKN extract and the precipitate thus obtained was collected by centrifugation. The precipitate was dissolved in 25 ml of 0.1M-phosphate buffer solution (pH 7.5) and applied on to a Sephadex G-100 column (diameter 2.6 cm, height 100 cm) which was previously buffered with the above-mentioned buffer solution. HUKN solution was thereby obtained.

The total activity of HUKN was 1,090 units (recovery rate of 56%) and the purity thereof was 290 units/mg (protein).

EXAMPLE 7

While stirring, 2N-hydrochloric acid was added to 20 liters of human urine from healthy male adults to adjust to pH 5.0. Two hundred grams of chitosan was contacted and stirred for one hour to thereby adsorb HUKN. Filtration was carried out and HUKN-adsorbed chitosan was obtained. Subsequently, the chitosan was sufficiently washed with pure water and extracted with 0.2M-tris-hydrochloric acid buffer solution (pH 9.0). Filtration was carried out and 800 ml of HUKN extract solution was thus obtained.

The total activity of HUKN was 2,856 units (recovery rate of 68%) and the purity thereof was 33 units/mg (protein).

The above HUKN extract was dialyzed against 0.1M-sodium hydrogencarbonate buffer solution (pH 9.0) containing 0.5M-sodium chloride and applied on to an aprotinine-Sepharose column (diameter 2.0 cm, height 20 cm) which was previously buffered with the above-mentioned buffer solution to thereby adsorb HUKN. Elution was carried out with 0.1M-acetic acid buffer solution (pH 3.5) containing 0.5M- sodium chloride and 20 ml of HUKN solution was thus obtained.

The total activity of HUKN was 2,142 units (recovery rate of 51%) and the purity thereof was 840 units/mg (protein).

In examples 1–7, units of HUKN extracted and purified from human urine by the present inventors were determined in accordance with the method of biological activity of vasodilator (Journal of Biochemistry, 58, 201, 1965), whereby measuring the increase in arterial blood flow following the injection of both standard and kallikrein preparations in saline using the dog. HUKN was assayed as directed in the assay method using Pro-Phe-Arg-MCA (Journal of Biochemistry 82, 1495, 1977), wherein the above HUKN was employed as the standard. The quantity of protein was determined by the method of Lowry-Folin employing bovine serum albumin as the standard.

We claim:

1. In the concentration and purification of human urine kallikrein, a process which comprises contacting chitosan with human urine at a pH from 4.0 to 7.0 to adsorb kallikrein in the urine on the chitosan, filtering off the chitosan from the urine and eluting kallikrein from the chitosan with an aqueous alkaline solution.

2. A process according to claim 1 wherein the aqueous alkaline solution has a pH from 8.0 to 12.0.

3. A process according to claim 1 wherein the filtered chitosan is washed with water before the elution.

4. A process according to claim 1 wherein the adsorption is carried out at common temperature.

5. A process according to claim 1 wherein the filtered chitosan is heated at about 60° C. in an aqueous solution having pH about 6 for not less than 10 hours before the elution to inactivate viruses which might contaminate the chitosan.

6. In the concentration and purification of human urine kallikrein, the steps of contacting chitosan with human urine at a pH from 4.0 to 7.0, filtering off the chitosan from the urine, washing the chitosan with water, and then, eluting kallikrein from the chitosan with an aqueous alkaline solution.

7. The steps according to claim 6 wherein the aqueous alkaline solution has a pH from 8.0 to 12.0.

* * * * *